US007835870B2

(12) United States Patent
Nair et al.

(10) Patent No.: US 7,835,870 B2
(45) Date of Patent: Nov. 16, 2010

(54) METHODS AND SYSTEMS FOR EVALUATING THE LENGTH OF ELONGATED ELEMENTS

(75) Inventors: Sankar Nair, Atlanta, GA (US); Soumendu Bhattacharya, Atlanta, GA (US); Vishwanath Natarajan, Atlanta, GA (US); Abhijit Chatterjee, Atlanta, GA (US)

(73) Assignee: Georgia Institute of Technology, Atlanta, GA (US)

( * ) Notice: Subject to any disclaimer, the term of this patent is extended or adjusted under 35 U.S.C. 154(b) by 452 days.

(21) Appl. No.: 11/264,452

(22) Filed: Nov. 1, 2005

(65) Prior Publication Data

US 2007/0099191 A1   May 3, 2007

(51) Int. Cl.
*G01N 33/48* (2006.01)
(52) U.S. Cl. .......................... 702/20; 324/635; 324/71.1
(58) Field of Classification Search ....................... None
See application file for complete search history.

(56) References Cited

U.S. PATENT DOCUMENTS

| 6,221,592 B1 * | 4/2001 | Schwartz et al. ............... 435/6 |
| 6,413,792 B1 * | 7/2002 | Sauer et al. .................... 438/49 |
| 2004/0033515 A1 * | 2/2004 | Cao et al. ....................... 435/6 |
| 2004/0144658 A1 * | 7/2004 | Flory ....................... 205/777.5 |

FOREIGN PATENT DOCUMENTS

EP     1329502     *   7/2003

OTHER PUBLICATIONS

Dukhin et al, Electrophoresis, vol. 26, p. 2149-2153, 2005.*
Demana et al. (Analytical Chemistry, vol. 63, p. 2795-2797, 1991).*
Andrew Marziali et al., "New DNA Sequencing Methods," Annual Review of Biomedical Engineering, 3: pp. 195-223, 2001.
Lilian T.C. França et al., "A Review of DNA Sequencing Techniques," Quarterly Reviews of Biophysics, 35 (2): pp. 69-200, 2002.
F. Sanger et al., "Nucleotide Sequence of Bacteriophage ΦX174 DNA," Nature, vol. 265 (5596), pp. 687-695, 1977.
Wenonah Vercoutere et al., "Biosensors for DNA Sequence Detection," Current Opinion in Chemical Biology, 6(6), pp. 816-822, 2002.
John J. Kasianowicz et al., "Simultaneous Multianalyte Detection with a Nanometer-Scale Pore," Analytical Chemistry, vol. 73, No. 10, 2001, pp. 2268-2272.
Hagan Bayley et al., "Stochastic Sensors Inspired by Biology," Nature, vol. 413, (6852), pp. 226-230, 2001.
B. Eisenberg, "Ion Channels as Devices," Journal of Computational Electronics, 2: pp. 245-249, 2003.
Scott A. Miller et al., "Redox Modulation of Electroosmotic Flow in a Carbon Nanotube Membrane," Journal of the American Chemical Society, 126: pp. 6226-6227, 2004.
Greg Khitrov, "Single DNA Molecules Detected by Nanopore Technology," MRS Bulletin, 28 (2); p. 96, 2003.
Amit Meller et al., "Rapid Nanopore Discrimination Between Single Polynucleotide Molecules," Proceedings of the National Academy of Sciences of the United States of America, vol. 97, No. 3, pp. 1079-1084, 2000.
Bert Sakmann et al., "Single-Channel Recording," $2^{nd}$ Edition, Plenum Press, New York, 1995, Chapter 12.
C.-M. Chen et al., "Nanopore Sequencing of Polynucleotides Assisted by a Rotating Electric Field," Applied Physics Letters, vol. 82, No. 8, pp. 1308-1310, 2003.
Sanjoy Mukherjee et al., "Phenomenology of the Growth of Single-Walled Aluminosilicate and Aluminogermanate Nanotubes of Precise Dimensions," Chemistry of Materials, vol. 17, No. 20, pp. 4900-4909, 2005.
Jiali Li et al., "Ion-beam Sculpting at Nanometre Length Scales," Nature, vol. 412, (6843), pp. 166-169, 2001.
M. Muthukumar, "Translocation of a Confined Polymer through a Hole," Physical Review Letters, vol. 86, No. 14, pp. 3188-3191, 2001.
Pu Tian et al., "Translocation of a Polymer Chain Across a Nanopore: A Brownian Dynamics Simulation Study," Journal of Chemical Physics, vol. 119, No. 21, pp. 11475-11483, 2003.
Elena Slonkina et al., "Polymer Translocation Through a Long Nanopore," Journal of Chemical Physics, vol. 118, No. 15, pp. 7112-7118, 2003.
H. Lodish et al., "Molecular Cell Biology," Fourth Edition, W.H. Freeman, New York, 2000, Chapter 4.
Serder Kuyucak et al., "Models of Permeation in Ion Channels," Reports of Progress in Physics, 64, pp. 1427-1472, 2001.
R. Pecora, "Spectral Distribution of Light Scattered by Monodisperse Rigid Rods," Journal of Chemical Physics, vol. 48, No. 9, pp. 4126-4128, 1968.

* cited by examiner

*Primary Examiner*—Karlheinz R Skowronek
(74) *Attorney, Agent, or Firm*—Merchant & Gould

(57) ABSTRACT

Systems and methods are disclosed for evaluating the length of elongated elements in a sample. The disclosed systems and methods may include using a direct current stimulus to determine a direct current base length region corresponding to at least a portion of the sample. Furthermore, the disclosed systems and methods may include using an alternating current stimulus to determine that the direct current base length region corresponds to a first set of elongated elements and a second set of elongated elements. The first set of elongated elements may have a first base length and the second set of elongated elements may have a second base length. The elongated elements may comprise, for example, chain molecules, deoxyribonucleic acid (DNA), ribonucleic acid (RNA), or proteins. Furthermore, the disclosed systems and methods may include measuring an ion current through a nanopore, the ion current produced by the alternating current stimulus.

11 Claims, 12 Drawing Sheets

```
function [f,A,] = decision(solution)

Input  solution with unknown composition of DNA
bases
Perform a DC simulation and generate histograms
Identify different regions
Compute mean base lengths for each region
(perform stimulus generation for each region
separately)

for Region R,
  Set initial frequency, amplitude and phase
  (f, A and  respectively)
  [N₁,N₂] = Calculate Base Pair(f,A,)

if more than one base found in region,
    S  DC Sensitivity(N₁,N₂)

while frequency not optimized
      i = current iteration
      S₁   AC Sensitivity(f+f,A,)
      S₂   AC Sensitivity(f-f,A,)
      Dᵢ   Calculate Direction(S1,S2)
      Sfᵢ  max(S1,S2);
      f_step  Decision(Sfᵢ,Sfᵢ₋₁,Dᵢ,Dᵢ₋₁,f)
      Change f by f_step
      if Sfᵢ>K.S or i > MaxIterations
        Frequency optimized
      end if
      i = i+1
    end while
    Repeat for A and  ...
    if not all optimized
      continue
    else
      Output  optimized f, A,
    end if end if
end for
```

*FIG. 10*

METHODS AND SYSTEMS FOR EVALUATING THE LENGTH OF ELONGATED ELEMENTS

This invention was made with Government support under Agreement No. CCF-0325555 awarded by the National Science Foundation. The Government has certain rights in this invention.

BACKGROUND OF THE INVENTION

I. Field of the Invention

The present invention generally relates to methods and systems for evaluating the length of elongated elements. More particularly, the present invention relates to evaluating the length of elongated elements using, for example, an alternating current stimulus.

II. Background Information

Size-separation and sequencing of chain-like biomolecules (e.g. single stranded deoxyribonucleic acid (DNA), ribonucleic acid (RNA), and proteins) is a process of vital importance in biotechnology and medicine. Sequencing speed is a bottleneck in genomics and allied disciplines. In particular, current DNA sequencing methods involve electrophoretic separation of DNA strands of varying sizes, generated by the well-established polymerase chain reaction (PCR) process. The PCR process generates DNA strands of varying lengths from the original sample, such that the length of a generated strand reflects the identity (e.g. A, C, G or T) of the base at the fluorescently labeled termination position. The sequencing problem is thus reduced to size-separating (or sizing) DNA strands. This step is carried out via electrophoresis in a gel or capillary bundle. The molecules are separated into bands by virtue of difference in their transport rates through the medium as a function of their size, under an applied electric field.

Efforts to substantially raise the throughput rates of these devices are impeded by the "short read length" problem (i.e. inefficient operation at long sequence lengths due to very slow transport of long strands through the medium.) In addition, the use of fluorescence-based optical techniques to detect the DNA bands increases the size and cost of DNA sequencing devices. However, overcoming the limitations of electrophoresis will result in a large technological impact, in terms of new applications such as "personalized medicine" (routine, patient-specific genome sequencing to diagnose genetic health risks), and fast genotyping of new pathogens or biological warfare agents to allow a rapid response.

In recent years, research at the biology-nanotechnology interface has shown potential for creating revolutionary advances in speed, efficiency, reliability, and portability of biomolecule sensors. An underlying advantage of a truly nano-scale biomolecule sensing technique is the ability to detect single molecules at a nanometer length scale and at very short time scales, using only small amounts of sample. Operation at short length and time scales would remove the transport limitations associated with electrophoresis technology. Of several proposed strategies for sizing DNA, the use of nano-scale ion channels is particularly attractive. The sensing element is a nanometer-scale pore (~2-5 nm in diameter and a few nm long) embedded in a substrate.

Different types of nanopores have been proposed or demonstrated for use in the above devices, and are currently under further development in several research groups. Conventional nanopores have used a direct current (DC) voltage to demonstrate the translocation of biomolecules through the pore. However, more sophisticated sensing protocols are needed to enable the processing of real samples in an efficient and reliable manner, and to optimize, for example, the characteristics of the sensor such as the sensitivity and signal-to-noise ratio.

In view of the foregoing, there is a need for methods and systems for evaluating the length of elongated elements comprising, but not limited to, chain biomolecules mixtures like DNA, RNA, or other proteins, more optimally. Furthermore, there is a need for evaluating the length of elongated elements using, for example, an alternating current stimulus. The elongated elements may comprise, but are not limited to, chain biomolecules mixtures like DNA, RNA, or other proteins.

Moreover, there is a need for methods and systems that include very high sensitivity (single molecule levels), extremely rapid and reversible response due to the short detection length and small time scales (c.a. 1 nm and 1 ms respectively), good signal-to-noise ratio even at low analyte concentrations, as single molecules are detected irrespective of concentration, and concurrent multiple-analyte sensing using arrays of nanopores. These needed methods and systems may increase sizing speeds from $10^4$-$10^5$ bases per day on a single electrophoresis instrument, to levels of $10^7$-$10^8$ bases per day (e.g. 3-4 orders of magnitude higher.) In addition, there is a need for methods and systems that may be combined with a circuit chip that analyzes the signals from the nanopore array, as well as a micro-fluidic system for handling input and output of analyte samples.

SUMMARY OF THE INVENTION

Consistent with embodiments of the present invention, systems and methods are disclosed for evaluating the length of elongated elements.

In accordance with one embodiment, a method for evaluating the length of elongated elements in a sample comprises using a direct current stimulus to determine a direct current base length region corresponding to at least a portion of the sample and using an alternating current stimulus to determine that the direct current base length region corresponds to a first set of elongated elements and a second set of elongated elements, the first set of elongated elements having a first base length and the second set of elongated elements having a second base length.

According to another embodiment, a system for evaluating the length of elongated elements in a sample comprises a memory storage for maintaining a database and a processing unit coupled to the memory storage, wherein the processing unit is operative to use a direct current stimulus to determine a direct current base length region corresponding to at least a portion of the sample and use an alternating current stimulus to determine that the direct current base length region corresponds to a first set of elongated elements and a second set of elongated elements, the first set of elongated elements having a first base length and the second set of elongated elements having a second base length.

In accordance with yet another embodiment, a computer-readable medium which stores a set of instructions which when executed performs a method for evaluating the length of elongated elements in a sample, the method executed by the set of instructions comprising using a direct current stimulus to determine a direct current base length region corresponding to at least a portion of the sample and using an alternating current stimulus to determine that the direct current base length region corresponds to a first set of elongated elements and a second set of elongated elements, the first set of elongated elements having a first base length and the second set of elongated elements having a second base length.

It is to be understood that both the foregoing general description and the following detailed description are exemplary and explanatory only, and should not be considered restrictive of the scope of the invention, as described and claimed. Further, features and/or variations may be provided in addition to those set forth herein. For example, embodiments of the invention may be directed to various combinations and sub-combinations of the features described in the detailed description.

BRIEF DESCRIPTION OF THE DRAWINGS

The accompanying drawings, which are incorporated in and constitute a part of this disclosure, illustrate various embodiments and aspects of the present invention. In the drawings:

FIG. 10 is a diagram illustrating pseudo-code for a diagnosis algorithm consistent with an embodiment of the present invention;

DETAILED DESCRIPTION

Figure 1:
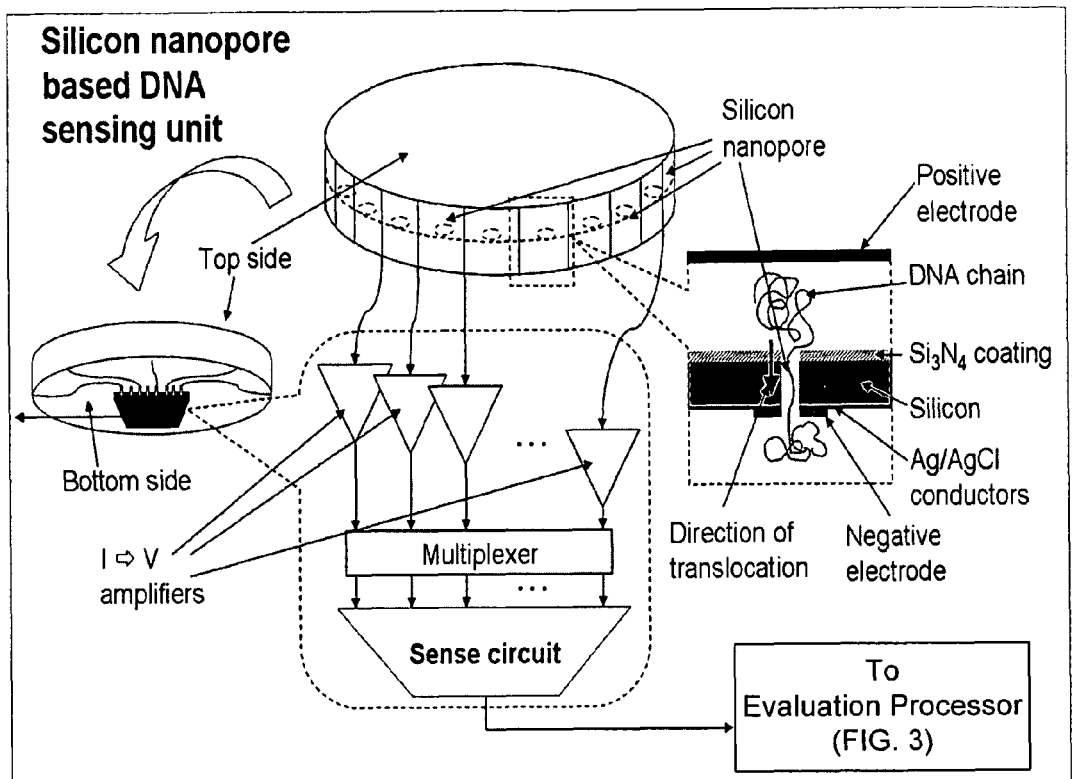
FIG. 1 is a diagram illustrating the operation of a sensing unit consistent with an embodiment of the present invention.

The following detailed description refers to the accompanying drawings. Wherever possible, the same reference numbers are used in the drawings and the following description to refer to the same or similar parts. While several exemplary embodiments and features of the invention are described herein, modifications, adaptations and other implementations are possible, without departing from the spirit and scope of the invention. For example, substitutions, additions or modifications may be made to the components illustrated in the drawings, and the exemplary methods described herein may be modified by substituting, reordering, or adding stages to the disclosed methods. Accordingly, the following detailed description does not limit the invention. Instead, the proper scope of the invention is defined by the appended claims.

Systems and methods consistent with embodiments of the present invention evaluate the length of elongated elements. Consistent with an embodiment of the invention, a diagnostic process for high-speed sizing of elongated elements by fabricated nanopores is provided. As stated above, the elongated elements may comprise, but are not limited to, chain biomolecules mixtures like DNA, RNA, or other proteins. The aforementioned are exemplary and other elongated elements may be evaluated. The diagnostic process is based on optimization of an externally applied electrical driving potential. An initial DC stimulus produces a coarse size distribution assay of the sample that can then be refined by an optimized AC stimuli specific to each region of the size distribution produced by the DC stimulus. In particular, an AC stimulus that is "tuned" to the time scale of the transport process considerably increases the system's performance.

FIG. 1 is a diagram illustrating the operation of a sensing unit 105 consistent with an embodiment of the present invention. As shown in FIG. 1, sensing occurs in sensing unit 105 by measuring the partial blockage of ionic current through a single nanopore as individual analyte molecules are driven through by an electric field. For chain molecules like DNA, RNA, and proteins, the duration of the current blockages correlate with the chain length. The physical basis of the present sensing technology is the measurement and interpretation of ionic current (pA to nA levels) through individually addressable nanoporous ion channels (of ~2-5 nm diameter) in a substrate (e.g. silicon nitride membrane of ~5 nm thickness). As shown in FIG. 1, when a biomolecule is driven through the nanopore, the ionic current is partially blocked. The duration of the current blockage correlates with the translocation time for the molecule through the nanopore, which is in turn is directly correlated to its length.

The electrodes that are used to supply the driving stimulus can be positioned close to the nanopore to detect currents. The nanopores and the electrodes may be submerged in a polymeric (e.g., teflon, acrylic) sample cell of fluid volume approximately 0.1-1 ml. Alternatively, this apparatus can be replaced with a nano/microfabricated system on a silicon chip, containing an array of individually addressable nanopores enclosed in fabricated micro-chambers with microelectrodes at appropriate locations.

Figure 2:
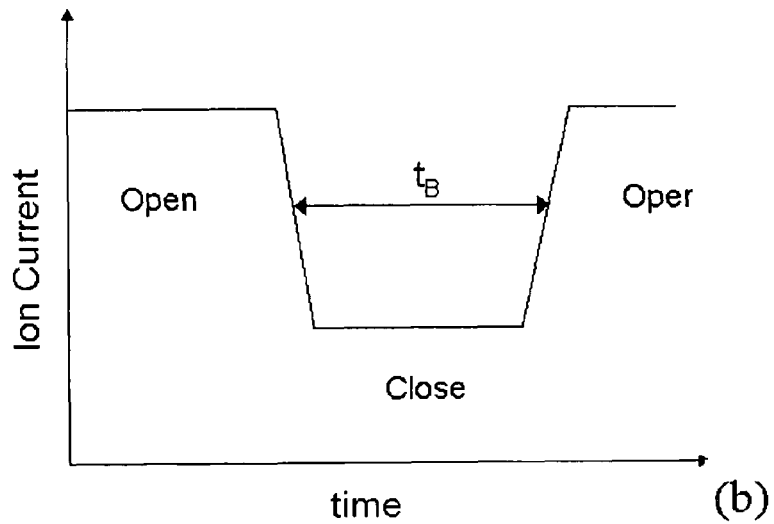
FIG. 2 is a diagram illustrating the operating principle of a sensing unit consistent with an embodiment of the present invention.

FIG. 2 illustrates the operating principle of sensing unit 105. In an "open" mode, the pore permits a high current. During translocation ("close"), the current is reduced to a low level due to partial nanopore blockage by the molecule. The blockage duration ($t_B$) correlates to the molecule length.

An embodiment consistent with the invention may comprise a system for evaluating the length of elongated elements. The system may comprise a memory storage for maintaining a database and a processing unit coupled to the memory storage. The processing unit may be operative to use a direct current stimulus to determine a direct current base length region corresponding to at least a portion of the sample. Furthermore, the processing unit may be operative to use an alternating current stimulus to determine that the direct current base length region corresponds to a first set of elongated elements and a second set of elongated elements. The first set of elongated elements may have a first base length and the second set of elongated elements may have g a second base length.

Figure 3:
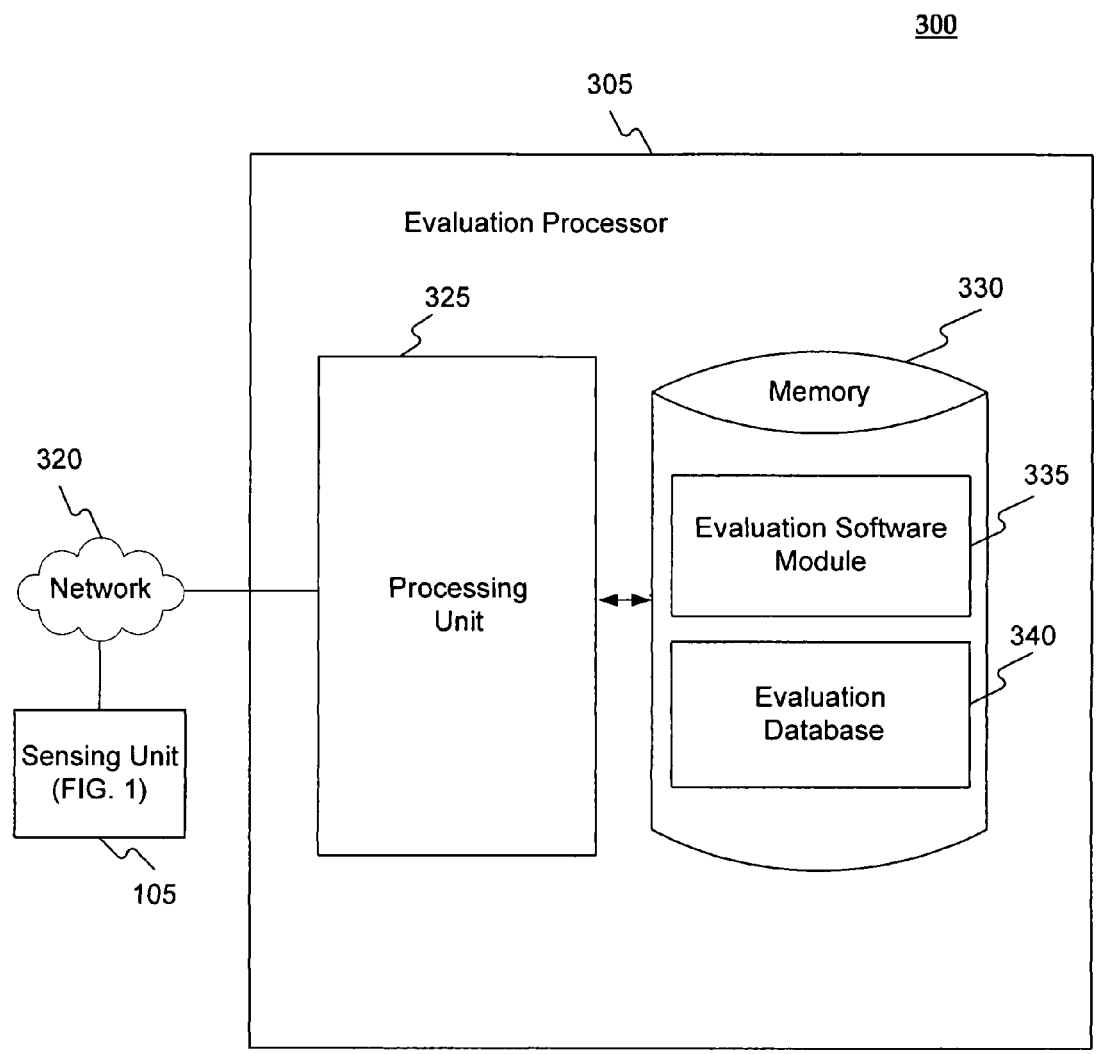
FIG. 3 is a block diagram of an exemplary evaluation processor consistent with an embodiment of the present invention.

Consistent with an embodiment of the present invention, the aforementioned memory, processing unit, and other components may be implemented in an evaluation system, such as an exemplary evaluation system 300 of FIG. 3. Any suitable combination of hardware, software, and/or firmware may be used to implement the memory, processing unit, or other components. By way of example, the memory, processing unit, or other components may be implemented with any of an evaluation processor 305, in combination with system 300. The aforementioned system and processor is exemplary and other systems and processors may comprise the aforementioned memory, processing unit, or other components, consistent with embodiments of the present invention.

By way of a non-limiting example, FIG. 3 illustrates system 300 in which the features and principles of the present invention may be implemented. As illustrated in the block diagram of FIG. 3, system 300 may include evaluation processor 305, sensing unit 105, and a network 320. As shown in FIG. 3, sensing unit 105 may obtain data regarding translocation time as described above and transmit this data to evaluation processor 305 over network 320. Moreover, evaluation processor 305 may be configured to control sensing unit 105's operation. Alternately, sensing unit 105 may be connected directly to evaluation processor 305.

As shown in FIG. 3, evaluation processor 305 may include a processing unit 325 and a memory 330. Memory 330 may include an evaluation software module 335 and an evaluation database 340. While executing on processing unit 325, evaluation software module 335 may perform processes for evaluating the length of elongated elements as described below, including, for example, one or more of the stages of exemplary method 900 described below with respect to FIG. 9.

Evaluation processor 305 ("the processor") included in system 300 may be implemented using a personal computer, network computer, mainframe, or other similar microcomputer-based workstation. The processor may though comprise any type of computer operating environment, such as hand-held devices, multiprocessor systems, microprocessor-based or programmable sender electronic devices, minicomputers, mainframe computers, and the like. The processor may also be practiced in distributed computing environments where tasks are performed by remote processing devices. Furthermore, any of the processor may comprise a mobile terminal, such as a smart phone, a cellular telephone, a cellular telephone utilizing wireless application protocol (WAP), personal digital assistant (PDA), intelligent pager, portable computer, a hand held computer, a conventional telephone, or a facsimile machine. The aforementioned systems and devices are exemplary and the processor may comprise other systems or devices.

Network 320 may comprise, for example, a local area network (LAN) or a wide area network (WAN). Such networking environments are commonplace in offices, enterprise-wide computer networks, intranets, and the Internet. When a LAN is used as network 320, a network interface located at any of the processor may be used to interconnect any of the processor. When network 320 is implemented in a WAN networking environment, such as the Internet, the processor may typically include an internal or external modem (not shown) or other means for establishing communications over the WAN. Further, in utilizing network 320 data sent over network 320 may be encrypted to insure data security by using known encryption/decryption techniques.

In addition to utilizing a wire line communications system as network 320, a wireless communications system, or a combination of wire line and wireless may be utilized as network 320 in order to, for example, exchange web pages via the Internet, exchange e-mails via the Internet, or for utilizing other communications channels. Wireless can be defined as radio transmission via the airwaves. However, it may be appreciated that various other communication techniques can be used to provide wireless transmission, including infrared line of sight, cellular, microwave, satellite, packet radio, and spread spectrum radio. The processor in the wireless environment can be any mobile terminal, such as the mobile terminals described above. Wireless data may include, but is not limited to, paging, text messaging, e-mail, Internet access and other specialized data applications specifically excluding or including voice transmission. For example, the processor may communicate across a wireless interface such as, for example, a cellular interface (e.g., general packet radio system (GPRS), enhanced data rates for global evolution (EDGE), global system for mobile communications (GSM)), a wireless local area network interface (e.g., WLAN, IEEE 802.11), a bluetooth interface, another RF communication interface, and/or an optical interface.

System 300 may also transmit data by methods and processes other than, or in combination with, network 320. These methods and processes may include, but are not limited to, transferring data via, diskette, flash memory sticks, CD ROM, facsimile, conventional mail, an interactive voice response system (IVR), or via voice over a publicly switched telephone network.

Consistent with an embodiment of the invention, as elongated elements (e.g. DNA molecules) are charged in an aqueous solution, an applied electrical potential forces them to move towards a nanopore and eventually pass through it. This nanopre passage is considered a "translocation event." The motion of the elongated elements under the influence of the applied electrical potential may be governed by three forces: i) electrical; ii) viscous drag; and iii) a rapidly fluctuating thermal force (random force). The random force may obey a normal distribution about a zero mean. The random force and the drag force may be highly correlated, because the molecular origin of both forces may be the same (e.g. bombardment of the biomolecule by solvent molecules.) The change in a channel resistance due to the passage of an elongated element through the nanopore causes a change (e.g. 50-75 pA) in an ionic current observed in the aqueous solution. The elongated element's length can be calculated based on the duration the channel (nanopore) blockage. This duration is the translocation time ($t_B$) for the elongated element.

The translocation time for elongated elements of the same length (under an applied DC potential) may show a stochastic variation and may follow a Gaussian distribution due to the random force effects operating during each translocation event. This may reduce sensing unit 105's resolution for distinguishing between two different chain lengths that are close in value. Even for two chains that can be clearly distinguished, the process may become time consuming and inefficient due to the measurement time required for improving the statistical quality of the data. Consistent with an embodiment of the invention an AC stimulus in addition to the applied DC potential may be used. By doing so, the difference between the translocation times of elongated elements of comparable lengths may be increased compared to using a DC stimulus alone.

A DNA molecule may be considered a rigid cylindrical rod. This is true at least because sensing unit 105 may operate at an appropriate pH and salt concentration of the DNA solution, in which conditions the DNA chains remain uncoiled and in an extended form by application of the electric field. Moreover, the motions along an x and y axis may be restricted and hence the only movement freedom degree for the molecule may be along a z-axis (along the nanopore's axis.) A DNA strand may have N bases (monomers), each of length l (~0.7 nm), giving a total length of L=Nl. The number of bases can be up to 10,000, for example. The DNA strand may have a diameter d (~1.5 nm.) Moreover, the length of the DNA chain is much greater than the length of the nanopore (~5 nm) so that the nanopore may be considered a hole of essentially zero thickness separating two chambers.

As stated above, forces acting on the elongated elements in the solution may comprise an electric force ($F_E$), a viscous drag force ($F_D$), and a random force ($F_R$). Regarding the electric force ($F_E$), within the solution, each base may hold approximately four electrons of charge. Thus, the total charge on, for example, a DNA strand may be Q=−4qN, where q=1.6×10$^{-19}$ Coulomb. With an assumed potential difference of V(ω, t) applied to the electrodes, the electrical force may be:

$$\vec{F}_E = Q \cdot \frac{V(\omega, t)}{s} \quad (1)$$

where s is the separation between the electrodes in sensing unit 105. Thus, the magnitude of electric force on an elongated element may be directly proportional to the molecule length.

Regarding the viscous drag force (FD), the magnitude of a drag force acting on an elongated element is given by:

$$\vec{F}_D = -M\gamma\vec{v} \quad (2)$$

where M is the mass of the elongated element (M=Nm, with m being the mass of a single monomer of the elongated element, ca. 330 a.m.u.), $\vec{v}$ is the velocity of the elongated element, and γ is the drag coefficient of the solution given by:

$$\gamma = \frac{3\pi\eta L}{M[\ln(L/d) + 1]} \quad (3)$$

where, η is the viscosity of water (0.0089 Poise). The drag force is proportional to N/ln(N), and increases with increasing elongated element length.

Random force ($F_R$), acting on an elongated element, may follow a gaussian distribution with zero mean and a variance given by 2MγkT/Δt. Here, k=1.38×10$^{-23}$ J/K is the Boltzmann constant and Δt is the time step used for numerical integration (e.g. ~1 ns). The random force may be related to the viscous force, as the drag coefficient γ appears in both force definitions.

Elongated element translocation through a nanopore in the presence of an electric field can be modeled using Newton's first law of motion:

$$M\frac{d\vec{v}}{dt} = \vec{F}_E + \vec{F}_D + \vec{F}_R \quad (4)$$

The initial velocity for the molecule may be obtained by equating its one-dimensional kinetic energy to the one-dimensional thermal energy ½kT:

$$\frac{1}{2}kT = \frac{1}{2}Mv_0^2 \rightarrow v_0 = \sqrt{kT/M} \quad (5)$$

Using equations (1) and (2), and substituting into equation (4), a differential equation may be written in v(t), with the initial condition given by equation (5). Algebraically manipulating equation (4) gives the translocation time under the influence of the forces aforementioned three forces. Due to the random force, the translocation times for molecules having the same length may be different for repeated simulation instances.

Figure 4:
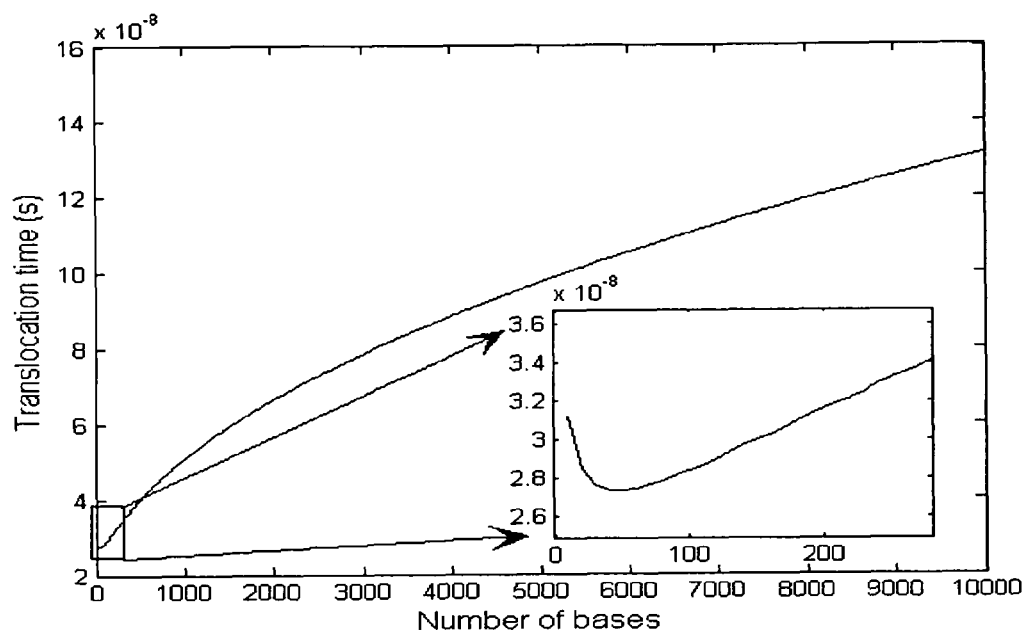
FIG. 4 is a diagram illustrating the variation of translocation time with change in base length (N) consistent with an embodiment of the present invention.

FIG. 4 is a diagram illustrating the variation of translocation time with change in base length (N) consistent with an embodiment of the present invention. For the example shown in FIG. 4, sensing unit 105 was first simulated with a 100 mV DC driving voltage. The differential equation (4) was solved to obtain the translocation time for an elongated element with different values of N. The variation of translocation time with change in base length (N) is shown in FIG. 4.

Figure 5:
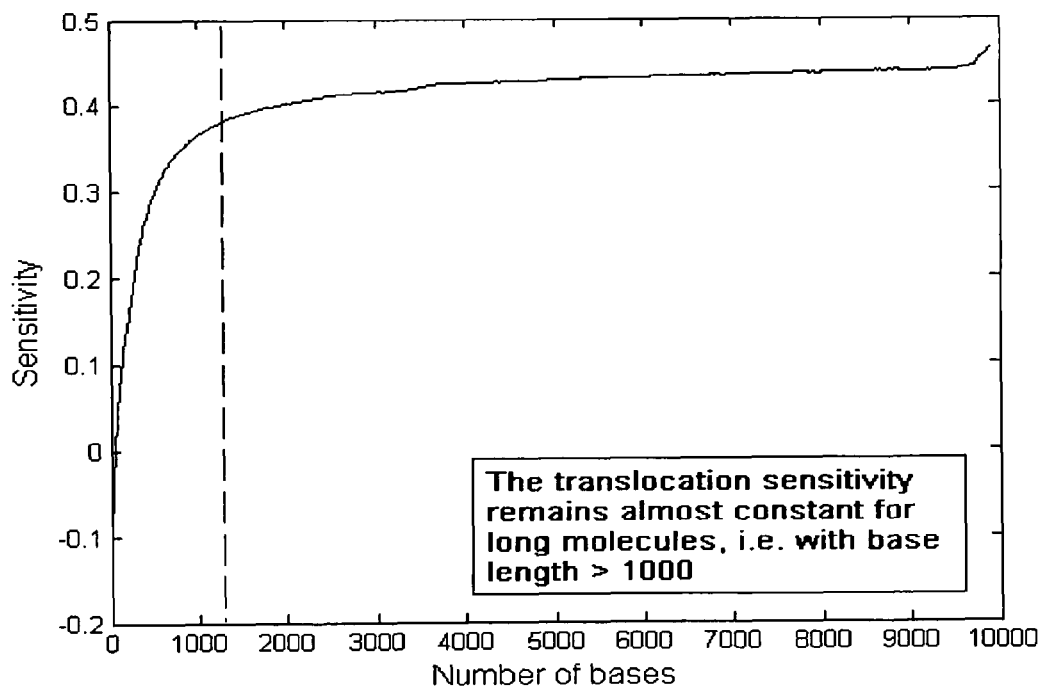
FIG. 5 is a diagram illustrating a DC sensitivity curve consistent with an embodiment of the present invention.

FIG. 5 is a diagram illustrating a DC sensitivity curve consistent with an embodiment of the present invention. The sensitivity of the translocation time of an elongated element to the lengths of the translocating molecules may be given by:

$$s = \frac{\Delta t_B/t_B}{\Delta N/N} \rightarrow \frac{N}{t_B} \cdot \frac{dt_B}{dN} \rightarrow \frac{d(\ln t_B)}{d(\ln N)} \quad (6)$$

As shown in FIG. 5, the sensitivity of sensing unit 105 is substantially constant for almost the entire range of elongated element (molecule) sizes investigated, and also becomes lower for short elongated elements (molecules.)

The DC stimulus may be used, for example, to diagnose the composition of a solution. Consequently, a number of histograms and area under each histogram may be calculated. The histograms may give an estimate of the different DNA bases constituting the solution. However, due to the effect of random forces, if two elongated elements (e.g. molecules) are almost the same length and the proportion of one elongated element (e.g. molecule) is much larger compared to the other, one elongated element may be completely masked in the histogram of the other elongated element. Accordingly, these factors may result in a reduced prediction accuracy when the DC stimulus is used.

Figure 6:
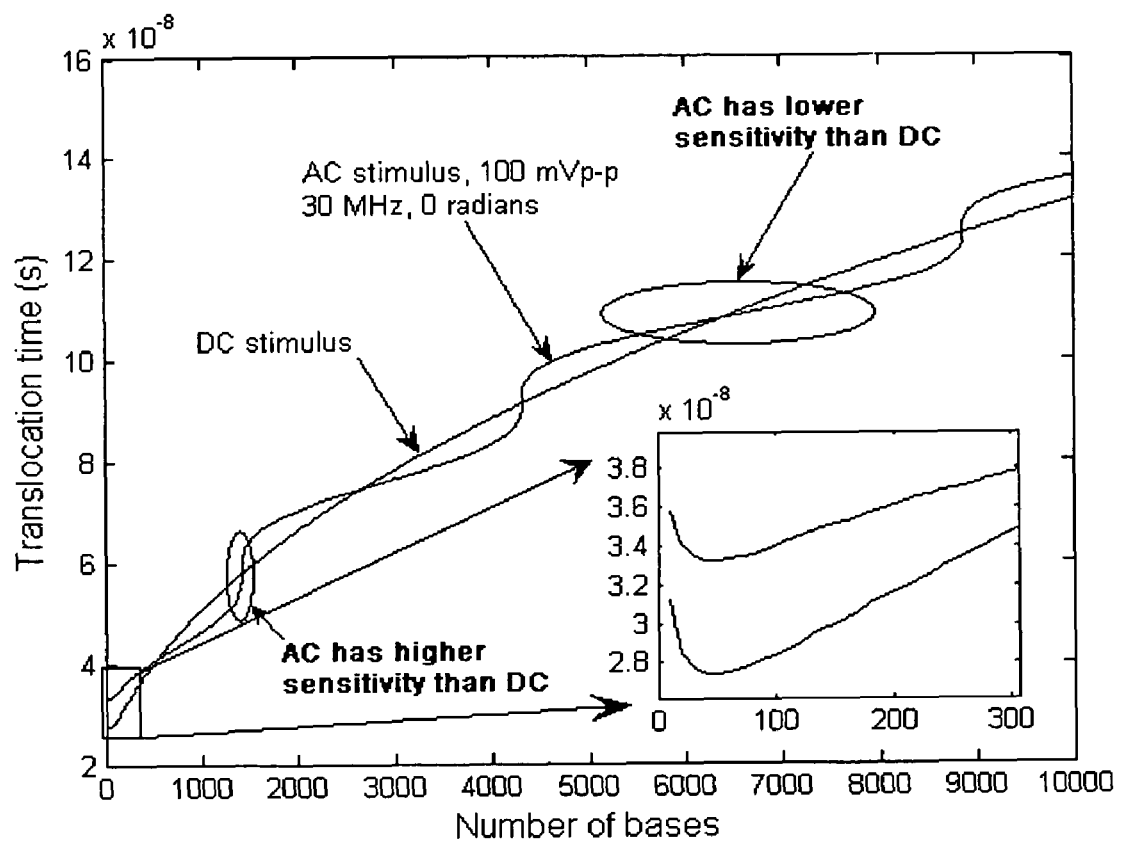
FIG. 6 is a diagram illustrating mean translocation time versus N for AC stimulus consistent with an embodiment of the present invention.

Consistent with an embodiment of the present invention, if a sinusoidal signal with carefully adjusted frequency, amplitude, and phase is added to the DC signal, the sensitivity for certain pairs of bases can be enhanced significantly. FIG. 6 is a diagram illustrating mean translocation time versus N for AC stimulus consistent with an embodiment of the present invention. As shown in FIG. 6, the translocation time vs. base length is plotted for an applied AC signal with the DC stimulus. For some regions of N, the slope of the translocation time curve (and hence the sensitivity) increases sharply when an AC stimulus is applied. However, for other regions, the sensitivity is lower than DC when an AC stimulus is applied.

Figure 7:
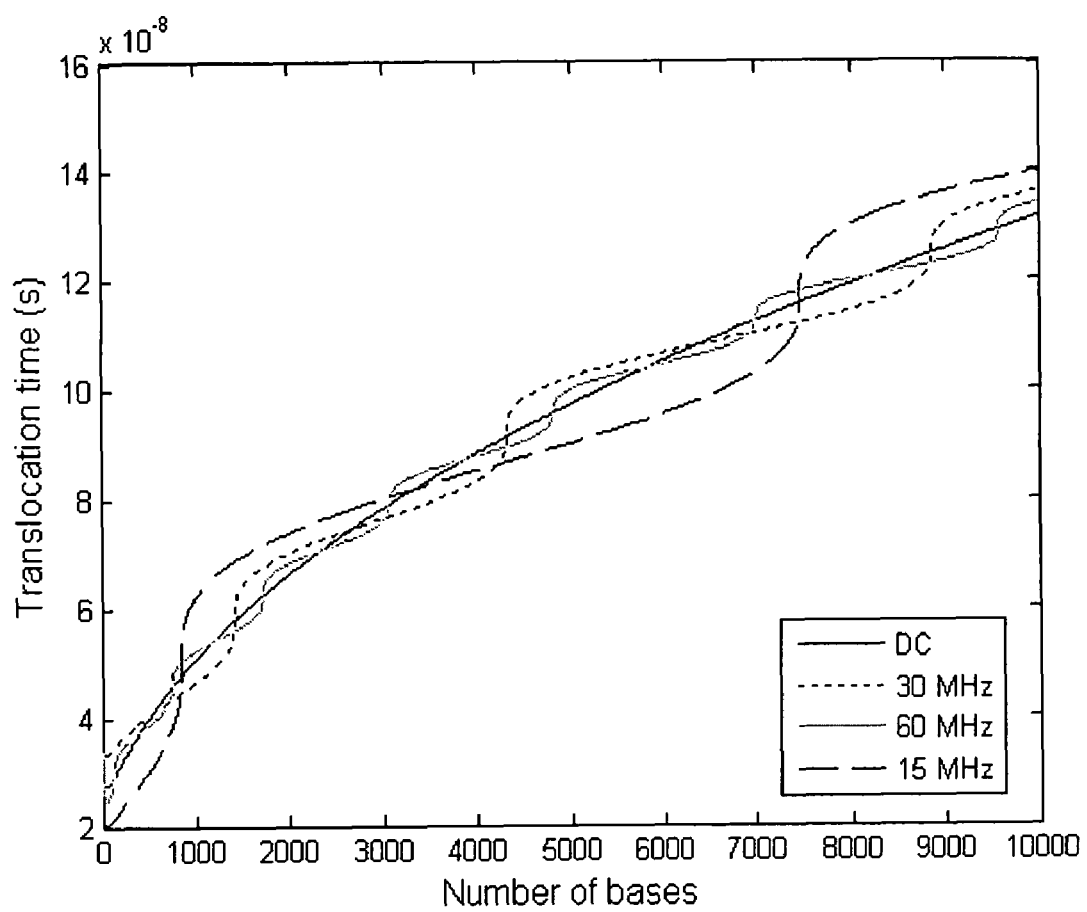
FIG. 7 is a diagram illustrating mean translocation time vs. N for different AC amplitudes with zero phase consistent with an embodiment of the present invention.

FIG. 7 is a diagram illustrating mean translocation time vs. N for different AC amplitudes with zero phase consistent with an embodiment of the present invention. As shown in FIG. 7, the sensitivity varies with the frequency, amplitude, phase, and the DC offset of the input AC and DC signals. The data in FIG. 7 shows that a particular combination of frequency, phase, amplitude, and DC offset values provides better performance than DC for one set of base lengths, and at the same time worse than DC for another set of base lengths.

Figure 8:
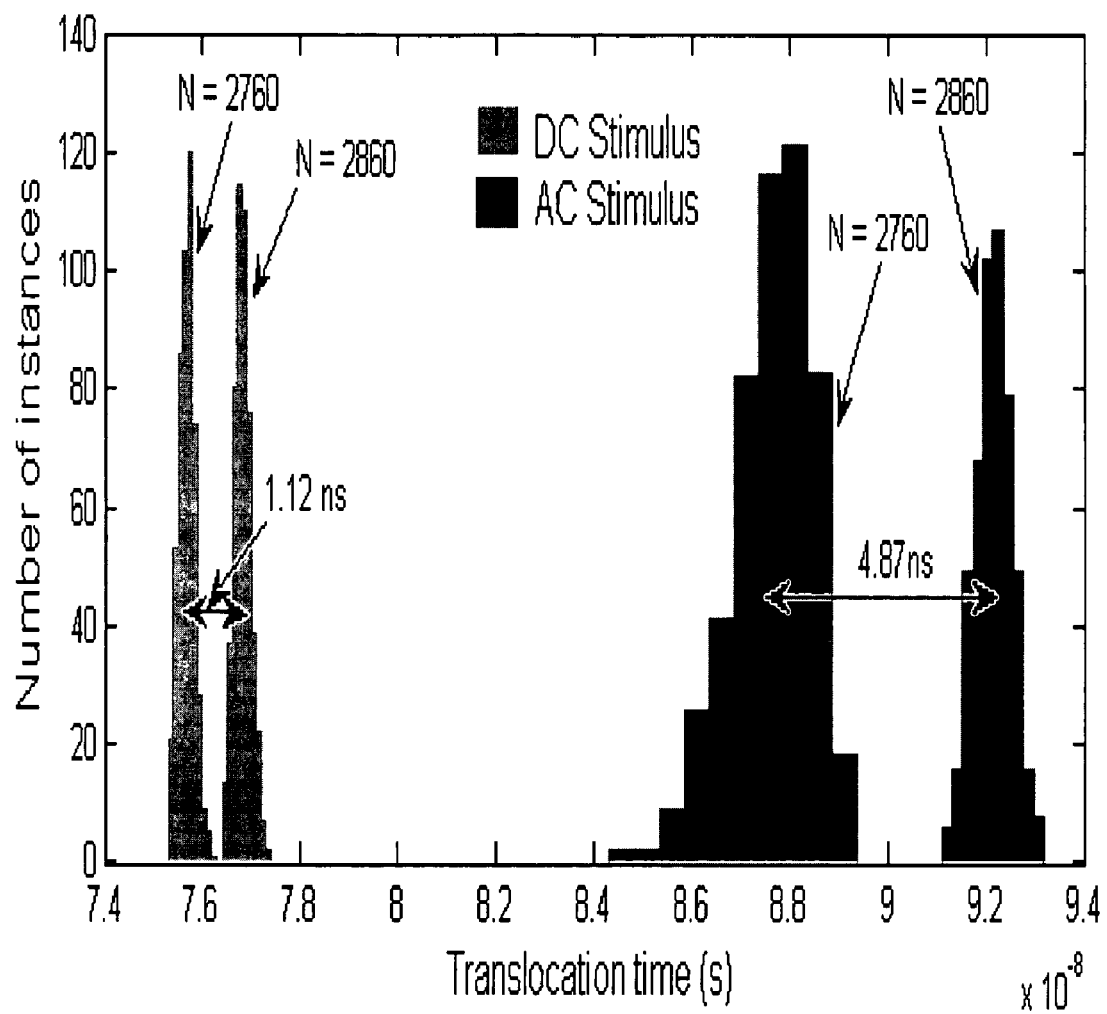
FIG. 8 is a diagram illustrating a histogram of stochastic translocation times for repeated translocation events of DNA molecules of two different base lengths consistent with an embodiment of the present invention.

FIG. 8 is a diagram illustrating a histogram of stochastic translocation times for repeated translocation events of DNA molecules of two different base lengths consistent with an embodiment of the present invention. FIG. 8 shows histograms of stochastic translocation times for repeated translocation events of DNA molecules of two different base lengths (2760 and 2860) under DC (left) and AC stimulus (right). As shown in FIG. 8, the introduction of an AC stimulus separates the two histograms better than the use of a DC stimulus, providing better resolution and diagnosis.

Figure 9:
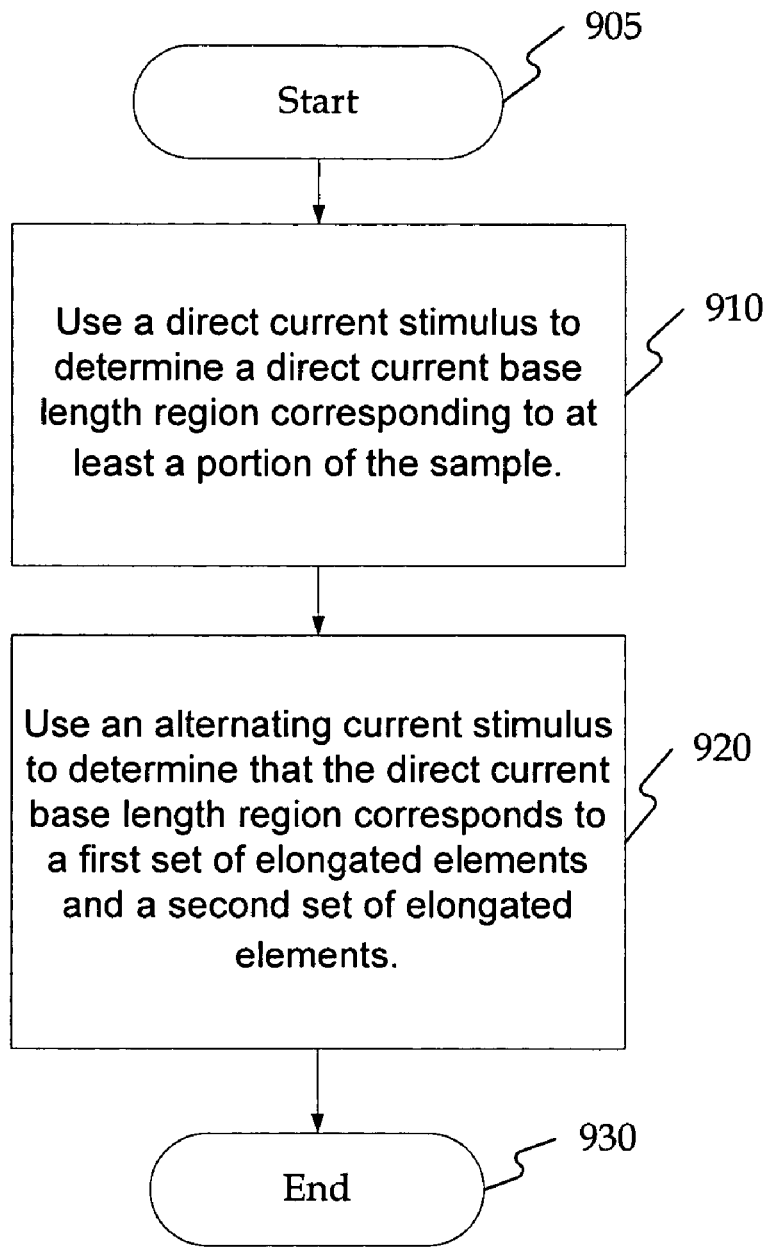
FIG. 9 is a flow chart of an exemplary method for evaluating the length of elongated elements in a sample consistent with an embodiment of the present invention.

FIG. 9 is a flow chart setting forth the general stages involved in an exemplary method 900 consistent with the invention for evaluating the length of elongated elements using system 300 of FIG. 3. Exemplary ways to implement the stages of exemplary method 900 will be described in greater detail below. Exemplary method 900 may begin at starting block 905 and proceed to stage 910 where evaluation processor 305 may use a DC stimulus to determine a DC base length region corresponding to at least a portion of the sample. FIG. 10 is a diagram illustrating pseudo-code for a diagnosis algorithm 1010 consistent with an embodiment of the present invention. For example, evaluation processor 305 may use diagnosis algorithm 1010 to optimize the frequency, amplitude, and phase of the AC stimulus to increase the sensitivity for a pair of molecules compared to DC. Algorithm 1010 consists of two main parts. The first part uses a DC stimulus to identify different base length regions (e.g. DC base length region) that may be present in the sample.

From stage 910, where evaluation processor 305 uses the direct current stimulus to determine the DC base length region corresponding to at least the portion of the sample, exemplary method 900 may advance to stage 920 where evaluation processor 305 may use an AC stimulus to determine that the DC base length region corresponds to a first set of elongated elements and a second set of elongated elements. The first set of elongated elements may have a first base length and the second set of elongated elements may have a second base length. For example, algorithm 1010's second part may optimize the AC stimulus for different regions (e.g. the DC base length region) identified by the DC stimulation. Each region may be investigated by optimizing the values of input parameters. These input parameters may comprise, but are not limited to, frequency, amplitude, and phase of the AC stimulus. These input parameters may be optimized to increase the sensitivity (e.g. the distance between the mean translocation times of the different elongated elements (e.g. DNA strands) of comparable lengths.)

The function "decision" used in algorithm 1010 may use a gradient search (steepest descent) algorithm to determine the optimal set of parameters (e.g. frequency, amplitude, and phase values for the AC stimulus.) Algorithm 1010 may also determine whether to increase or decrease the optimization parameters and the step size for the same. In addition, algorithm 1010 may maintain a history of the optimization steps. At some point, if the optimization parameters move away from a target value, algorithm 1010 may revert to the previous point where the best sensitivity was obtained, and change the search direction.

Moreover, algorithm 1010 may target a sensitivity attention (using AC stimulus) equal to, for example, K times that for a DC stimulus. K may be a user-specified performance enhancement factor, set to a value of 3, for example. The algorithm 1010 may stop when each of the optimization parameters achieve this condition. After evaluation processor 305 uses the alternating current stimulus to determine that the direct current base length region corresponds to the first set of elongated elements and the second set of elongated elements in stage 920, exemplary method 900 may then end at stage 930.

Operational Example

Figure 11:
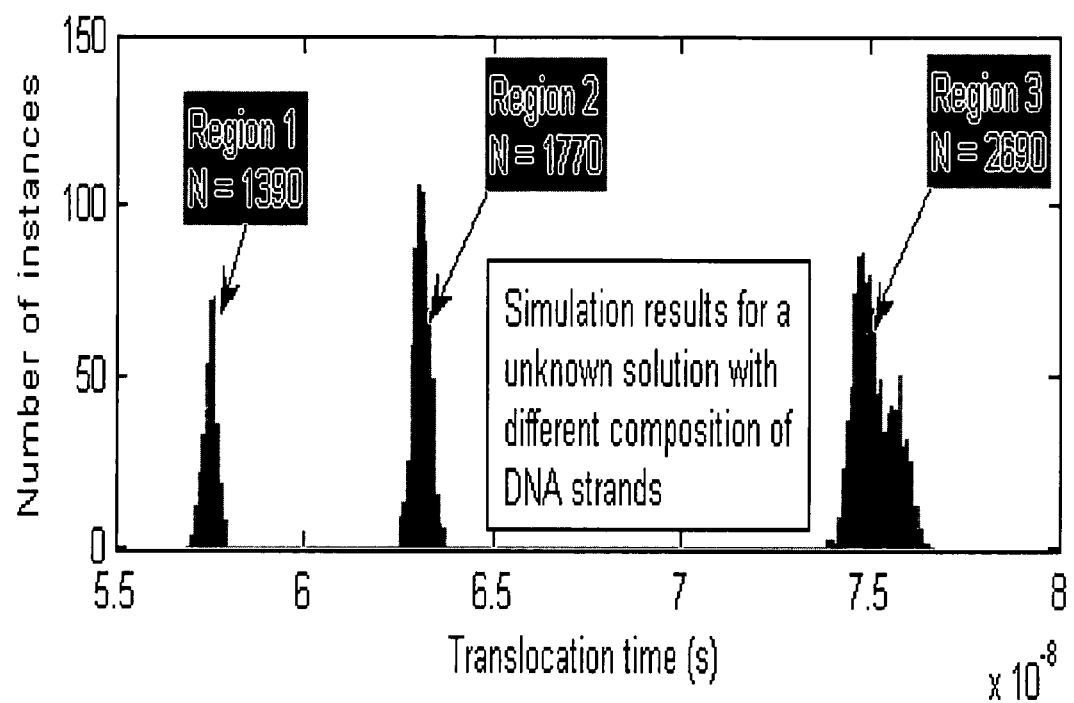
FIG. 11 is a diagram illustrating histograms for an operational example consistent with an embodiment of the present invention.

Consistent with an operational example, algorithm 1010 may be used to simulate and diagnose a solution of unknown bases. For example, a solution with base lengths 1390, 1760, 2680, and 2760 may be used. Sensing unit 105 output from this solution may be simulated with a DC stimulus of 100 mV. FIG. 11 is a diagram illustrating histograms for an operational example consistent with an embodiment of the present invention. As shown in FIG. 11, while the two smaller molecules were easily distinguished, the molecules having lengths 2680 and 2760 bases were not distinguishable from each other. Therefore, three regions (Region 1, Region 2, and Region 3) could be identified for separate optimization analysis to find the optimal AC stimulus for each region. In addition, the mean of each region and the corresponding base lengths were determined. In other words, four bases were present, but two of the bases (Region 3) were not distinguishable from each other.

Figure 12:
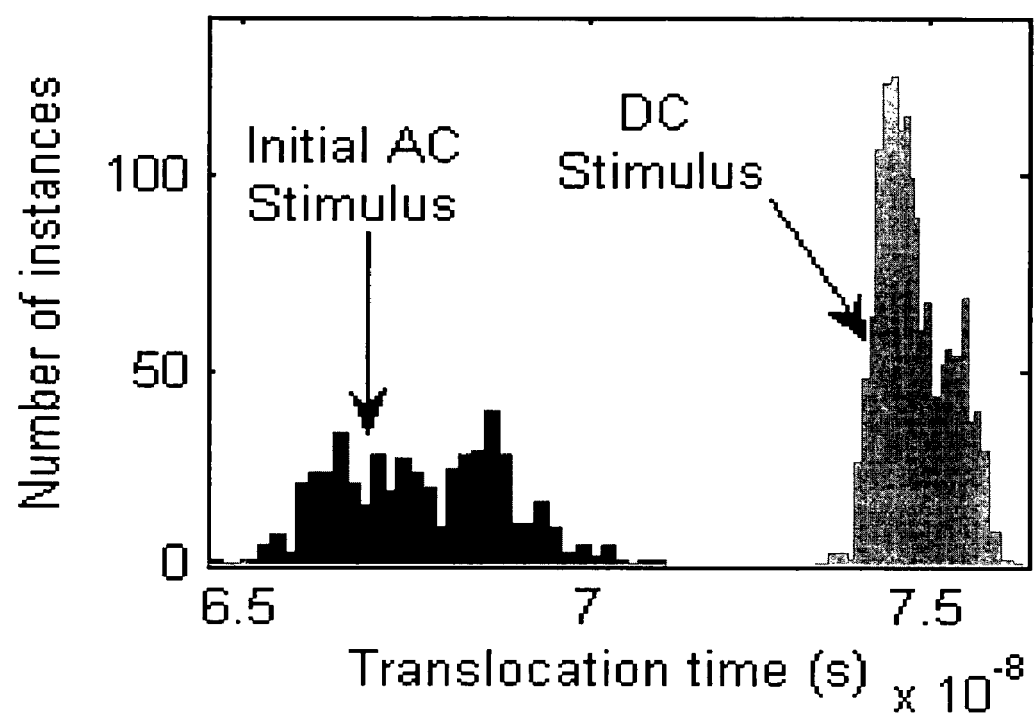
FIG. 12 is a diagram illustrating translocation time histograms in Region 3 for the DC and the initial AC stimulus applied consistent with an embodiment of the present invention.

Next, each region shown in FIG. 11 was simulated with an AC stimulus. The initial AC frequency choice for stimulus was calculated from the inverse of the mean translocation time of the region. The AC stimulus' initial amplitude was chosen to be 50 mV. Regions 1 and 2 contained only one type of strand each and did not show any more molecule lengths when simulated with the AC stimulus. FIG. 12 is a diagram illustrating translocation time histograms in Region 3 for the DC and the initial AC stimulus applied consistent with an embodiment of the present invention. As shown in FIG. 12, Region 3, however, showed significant splitting when the above-mentioned AC stimulus was applied.

Figure 13:
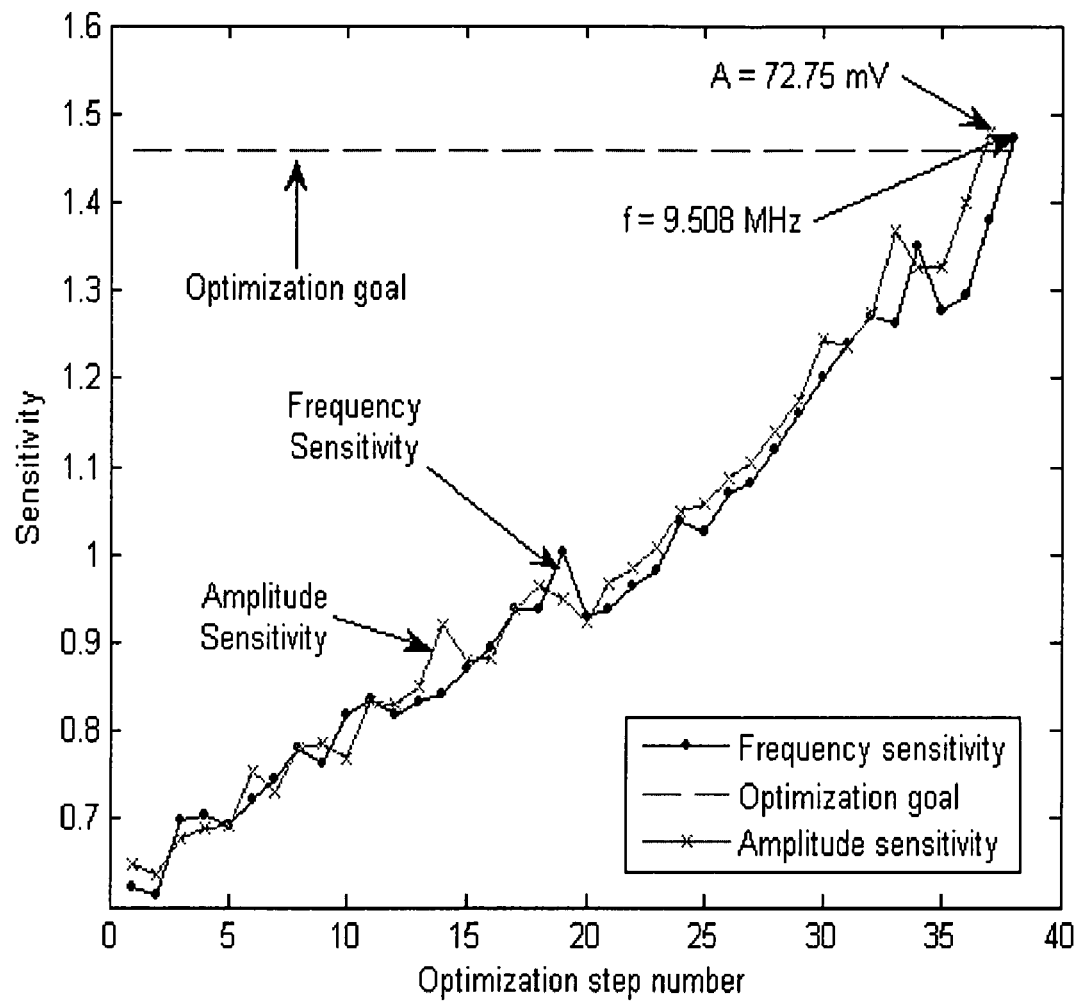
FIG. 13 is a diagram illustrating a change in sensitivity values with progress in optimization consistent with an embodiment of the present invention.

Algorithm 1010 was then applied to refine the sensitivity in Region 3. It can be observed that the phase and the frequency opposed each other during optimization, so phase was not optimized further and was set at zero for all applied AC stimuli. The DC stimulus showed a spread of the translocation times by 2.9 ns (FIG. 11), while the initial AC stimulus (f=13 MHz, A=50 mV) doubled the spread to 6.1 ns. FIG. 13 is a diagram illustrating a change in sensitivity values with progress in optimization consistent with an embodiment of the present invention. As shown in FIG. 12, sensitivity improved as the optimization proceeds till the desired enhancement factor was obtained.

Figure 14:
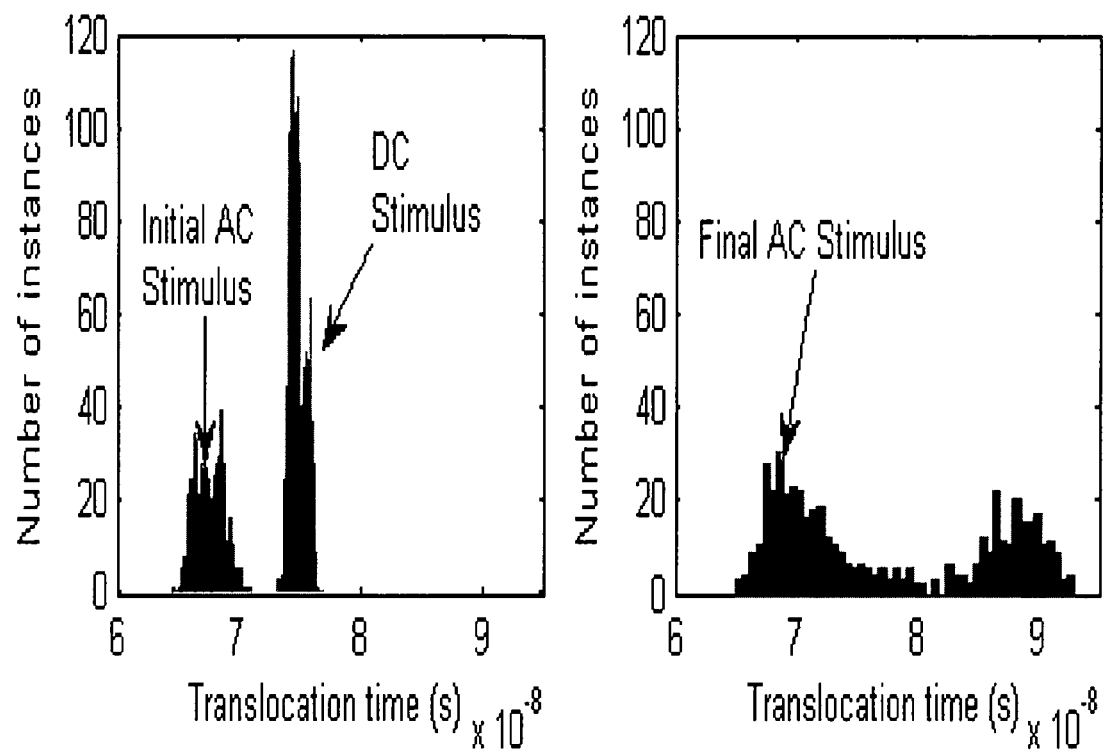
FIG. 14 is a diagram illustrating performance for DC and the initial AC stimulus and the optimized AC stimulus consistent with an embodiment of the present invention.

FIG. 14 is a diagram illustrating performance for DC and the initial AC stimulus (left) and the optimized AC stimulus (right) consistent with an embodiment of the present invention. The final stimulus (f=9.5 MHz, A=72.75 mV) obtained from the optimization algorithm shows a spread of 27.6 ns, about ten times the spread for a DC stimulus. Using this stimulus, the two molecules can be easily distinguished in the histogram shown in FIG. 14. Thus, the AC stimulus not only helps diagnosing the hidden bases within each region, it also increases the resolution of the diagnosis process significantly. This operational example shows the potential for model and/or algorithm based diagnostic approaches towards optimizing the performance of this technology. The short time scales make it feasible to implement the optimization process "on the fly" during operation, to analyze, for example, DNA mixtures of arbitrary complexity.

Furthermore, the invention may be practiced in an electrical circuit comprising discrete electronic elements, packaged or integrated electronic chips containing logic gates, a circuit utilizing a microprocessor, or on a single chip containing electronic elements or microprocessors. The invention may also be practiced using other technologies capable of performing logical operations such as, for example, AND, OR, and NOT, including but not limited to mechanical, optical, fluidic, and quantum technologies. In addition, the invention may be practiced within a general purpose computer or in any other circuits or systems.

The present invention may be embodied as systems, methods, and/or computer program products. Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention are described above with reference to block diagrams and/or operational illustrations of methods, systems, and computer program products according to embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

While certain features and embodiments of the invention have been described, other embodiments of the invention may exist. Furthermore, although embodiments of the present invention have been described as being associated with data stored in memory and other storage mediums, aspects can also be stored on or read from other types of computer-readable media, such as secondary storage devices, like hard disks, floppy disks, or a CD-ROM, a carrier wave from the Internet, or other forms of RAM or ROM. Further, the steps of the disclosed methods may be modified in any manner, including by reordering steps and/or inserting or deleting steps, without departing from the principles of the invention.

It is intended, therefore, that the specification and examples be considered as exemplary only, with a true scope and spirit of the invention being indicated by the following claims and their full scope of equivalents.

What is claimed is:

1. A system for evaluating the length of biopolymers in a sample, the system comprising:
    a memory storage for maintaining a database; and
    a processing unit coupled to the memory storage, wherein the processing unit is operative to:
        use a direct current stimulus to determine a direct current base length region corresponding to at least a portion of the sample, the direct current base length region appearing to correspond to biopolymers of only one length after the direct current stimulus is used;
        determine an initial value for at least one alternating current stimulus characteristic;
        use a combination stimulus comprising a combination of the direct current stimulus and an alternating current stimulus to determine that the direct current base length region corresponds to a first set of biopolymers and a second set of biopolymers, the first set of biopolymers having a first base length and the second set of biopolymers having a second base length, wherein the processing unit being operative to use the combination stimulus comprises the processing unit operative to iteratively optimize the at least one alternating current stimulus characteristic, starting with the determined initial value, to increase the sensitivity of the determined direct current base length region wherein the processing unit being operative to iteratively optimize comprises the processing unit being operative to iteratively adjust the alternating current stimulus characteristic from the determined initial value to increase a difference between a mean translocation time corresponding to the first set of biopolymers and a mean translocation time corresponding to the second set of biopolymers;
        use the at least one optimized alternating current stimulus characteristic value to determine a length of a biopolymer in the sample; and
        output the determined length of the biopolymer.

2. The system of claim 1, wherein the processing unit operative to use the combination stimulus to determine that the direct current base length region corresponds to the first set of biopolymers and the second set of biopolymers further comprises at least one of the first set of biopolymers and the second set of biopolymers comprising at least one of the following: chain molecules, deoxyribonucleic acid (DNA), ribonucleic acid (RNA), and proteins.

3. The system of claim 1, wherein the processing unit operative to use the combination stimulus to determine that the direct current base length region corresponds to the first set of biopolymers and the second set of biopolymers comprises the processing unit operative to measure an ion current through a nanopore, the ion current produced by the alternating current stimulus.

4. The system of claim 1, wherein the at least one alternating current stimulus characteristic comprises one of the following characteristics: a frequency associated with the alternating current stimulus, an amplitude associated with the alternating current stimulus, and a phase associated with the alternating current stimulus.

5. The system of claim 1, wherein the processing unit operative to iteratively adjust the alternating current stimulus comprises the processing unit operative to use a gradient search to optimize the at least one alternating current stimulus characteristic to produce a predetermined sensitivity value, the at least one alternating current stimulus characteristic comprising one of the following characteristics: a frequency associated with the alternating current stimulus, an amplitude associated with the alternating current stimulus, and a phase associated with the alternating current stimulus.

6. A system of claim 1, wherein the alternating current stimulus is applied in an alternating current stimulus direction that is substantially the same as a direction that the first set of biopolymers and the second set of biopolymers translocate through a nanopore.

7. The system of claim 1, wherein the combination stimulus is derived using a realistic physics-based model.

8. The system of claim 1, wherein the processing unit being operative to iteratively adjust the alternating current stimulus characteristic comprises the processing unit being operative to iteratively adjust the alternating current stimulus characteristic from the determined initial value in an intelligent manner based upon input from a realistic physics-based model to eliminate all but a limited subset of a fundamentally infinite number of possible stimulus choices.

9. The system of claim 1, wherein iteratively optimizing the at least one alternating current stimulus characteristic comprises iteratively optimizing using a number of iterations equal to a user-specified performance enhancement factor.

10. A system for evaluating the length of biopolymers in a sample, the system comprising:
a memory storage for maintaining a database; and
a processing unit coupled to the memory storage, wherein the processing unit is operative to:
use a direct current stimulus to determine a direct current base length region corresponding to at least a portion of the sample, the direct current base length region appearing to correspond to biopolymers of only one length after the direct current stimulus is used;
determine a first initial value for a first alternating current stimulus characteristic value corresponding to an alternating current stimulus, the first alternating current stimulus characteristic value comprising one of the following characteristics: a frequency associated with the alternating current stimulus, an amplitude associated with the alternating current stimulus, and a phase associated with the alternating current stimulus;
use a combination stimulus comprising a combination of the direct current stimulus and the alternating current stimulus to iteratively optimize the first alternating current stimulus characteristic value for the alternating current stimulus, starting with the determined first initial value, to increase the sensitivity of the direct current base length region wherein the processing unit being operative to iteratively optimize the first alternating current stimulus characteristic value comprises the processing unit being operative to iteratively adjust the first alternating current stimulus characteristic value to increase a difference between a mean translocation time corresponding to a first set of biopolymers in the sample and a mean translocation time corresponding to a second set of biopolymers in the sample;
determine a second initial value for a second alternating current stimulus characteristic value corresponding to the alternating current stimulus, the second alternating current stimulus characteristic value comprising one of the following characteristics: the frequency associated with the alternating current stimulus, the amplitude associated with the alternating current stimulus, and the phase associated with the alternating current stimulus, wherein the first alternating current stimulus characteristic value and the second alternating current stimulus characteristic value correspond to different characteristics;
use the combination stimulus comprising the combination of the direct current stimulus and the alternating current stimulus to iteratively optimize the second alternating current stimulus characteristic value for the alternating current stimulus, starting with the determined second initial value, to increase the sensitivity of the direct current base length region wherein the processing unit being operative to iteratively optimize the second alternating current stimulus characteristic value comprises the processing unit being operative to iteratively adjust the second alternating current stimulus characteristic value to increase the difference between the mean translocation time corresponding to the first set of biopolymers in the sample and the mean translocation time corresponding to a second set of biopolymers in the sample;
determine a third initial value for a third alternating current stimulus characteristic value corresponding to the alternating current stimulus, the third alternating current stimulus characteristic value comprising one of the following characteristics: the frequency associated with the alternating current stimulus, the amplitude associated with the alternating current stimulus, and the phase associated with the alternating current stimulus, wherein the first alternating current stimulus characteristic value, the second alternating current stimulus characteristic value, and the third alternating current stimulus characteristic value correspond to different characteristics;
use the combination stimulus comprising the combination of the direct current stimulus and the alternating current stimulus to iteratively optimize the third alternating current stimulus characteristic value for the alternating current stimulus, starting with the determined third initial value, to increase the sensitivity of the direct current base length region wherein the processing unit being operative to iteratively optimize the third alternating current stimulus characteristic value comprises the processing unit being operative to iteratively adjust the third alternating current stimulus characteristic value to increase the difference between the mean translocation time corresponding to the first set of biopolymers in the sample and the mean translocation time corresponding to the second set of biopolymers in the sample;
use the optimized first alternating current stimulus characteristic value, the optimized second alternating current stimulus characteristic value, and the optimized third alternating current stimulus characteristic value to determine a length of a biopolymer in the sample; and
output the determined length of the biopolymer.

11. The system of claim 10, wherein the alternating current stimulus is applied in an alternating current stimulus direction that is substantially the same as a direction that the first set of biopolymers and the second set of biopolymers translocate through a nanopore.

* * * * *